US008267912B2

(12) United States Patent
Ferris

(10) Patent No.: US 8,267,912 B2
(45) Date of Patent: Sep. 18, 2012

(54) INFUSION BAG WITH NEEDLELESS ACCESS PORT

(76) Inventor: Richard George Ferris, Valley View, TX (US)

( * ) Notice: Subject to any disclaimer, the term of this patent is extended or adjusted under 35 U.S.C. 154(b) by 770 days.

(21) Appl. No.: 12/117,056

(22) Filed: May 8, 2008

(65) Prior Publication Data

US 2009/0030396 A1 Jan. 29, 2009

Related U.S. Application Data

(60) Provisional application No. 60/952,009, filed on Jul. 26, 2007.

(51) Int. Cl.

| | |
|---|---|
| ***A61B 19/00*** | (2006.01) |
| *A61M 5/32* | (2006.01) |
| *B65D 33/06* | (2006.01) |
| *B65D 33/00* | (2006.01) |
| *B65D 33/16* | (2006.01) |
| *B65D 30/24* | (2006.01) |
| *B65D 33/01* | (2006.01) |
| *B65D 25/08* | (2006.01) |
| *B65D 79/00* | (2006.01) |

(52) U.S. Cl. ............ 604/408; 604/403; 604/415; 383/6; 383/41; 383/42; 383/45; 383/100; 383/105; 383/904; 383/907; 206/219; 206/527

(58) Field of Classification Search .................. 604/408, 604/403, 415, 82, 93.01; 206/219, 527; 383/6, 383/41, 42, 45, 100, 105, 904, 907; 422/44
See application file for complete search history.

(56) References Cited

U.S. PATENT DOCUMENTS

| | | | | |
|---|---|---|---|---|
| 3,058,464 | A * | 10/1962 | Broman | 422/47 |
| 3,915,212 | A * | 10/1975 | Bujan et al. | 604/408 |
| 4,369,781 | A | 1/1983 | Gilson et al. | |
| 4,452,473 | A | 6/1984 | Ruschke | |
| 4,466,888 | A * | 8/1984 | Verkaart | 210/232 |
| 4,550,825 | A * | 11/1985 | Sutryn et al. | 206/222 |
| 4,622,032 | A * | 11/1986 | Katsura et al. | 604/122 |
| 4,639,019 | A | 1/1987 | Mittleman | |
| 4,643,713 | A * | 2/1987 | Viitala | 604/6.15 |
| 4,717,377 | A * | 1/1988 | Fukasawa | 604/6.15 |
| 4,723,956 | A * | 2/1988 | Schnell et al. | 604/414 |
| 4,734,269 | A * | 3/1988 | Clarke et al. | 96/156 |
| 4,795,457 | A * | 1/1989 | Cooney | 604/408 |

(Continued)

OTHER PUBLICATIONS

Robertsite® Needlefree Valves, Halkey-Roberts, Oct. 2004.

*Primary Examiner* — Patricia Bianco
*Assistant Examiner* — Adam Marcetich
(74) *Attorney, Agent, or Firm* — Leason Ellis LLP

(57) ABSTRACT

An infusion bag according to one exemplary embodiment includes a body having an interior space for holding a fluid. The interior space is defined by a pair of side walls and an inner wall and an opposite bottom wall. The inner wall extends across the body from one side wall to the other side wall such that a first angle α1 is formed between a first end of the inner wall and one side wall and a second angle α2 is formed between a second end of the inner wall and the other side wall. The first angle is different from the second angle. The bag also includes a needleless port that is in fluid communication with the interior and is configured to sealingly mate with an external device. The needleless port is disposed in an upper corner of the body.

19 Claims, 6 Drawing Sheets

U.S. PATENT DOCUMENTS

| | | | | |
|---|---|---|---|---|
| 4,838,875 | A | 6/1989 | Somor | |
| D303,013 | S | 8/1989 | Konopka | |
| 4,952,210 | A | 8/1990 | Alchas | |
| 4,976,708 | A * | 12/1990 | Oshiyama | 604/408 |
| 5,163,922 | A | 11/1992 | McElveen, Jr. et al. | |
| 5,391,150 | A | 2/1995 | Richmond | |
| 5,464,399 | A | 11/1995 | Boettger | |
| 5,527,007 | A * | 6/1996 | Weilbacher | 248/304 |
| 5,624,414 | A | 4/1997 | Boettger | |
| 5,645,538 | A | 7/1997 | Richmond | |
| 5,810,793 | A | 9/1998 | Boettger | |
| 5,848,994 | A | 12/1998 | Richmond | |
| 6,019,751 | A * | 2/2000 | Gabbard et al. | 604/408 |
| 6,039,719 | A * | 3/2000 | Wieslander et al. | 604/410 |
| 6,068,617 | A | 5/2000 | Richmond | |
| 6,082,585 | A * | 7/2000 | Mader et al. | 222/83 |
| 6,106,502 | A | 8/2000 | Richmond | |
| 6,337,049 | B1 * | 1/2002 | Tamari | 422/44 |
| 6,872,197 | B1 * | 3/2005 | Witowski | 604/408 |
| 2003/0040708 | A1 | 2/2003 | Rogers et al. | |
| 2005/0059952 | A1 | 3/2005 | Giuliano et al. | |
| 2007/0211967 | A1 * | 9/2007 | Murray | 383/38 |
| 2007/0217717 | A1 * | 9/2007 | Murray | 383/38 |
| 2008/0172022 | A1 * | 7/2008 | Poo et al. | 604/408 |

* cited by examiner

INFUSION BAG WITH NEEDLELESS ACCESS PORT

CROSS-REFERENCE TO RELATED APPLICATION

The present application claims the benefit of U.S. 60/952,009, filed Jul. 26, 2007, which is hereby incorporated by reference in its entirety.

TECHNICAL FIELD

The present invention relates to devices and systems for administering fluids, such as medicinal fluids to patients and in particular, to an infusion bag that includes one or more needleless access ports that each includes a quick disconnect and connect coupling member that ensures sterility for use in association with conduits, syringes and other such equipment commonly associated with medicinal liquid therapies.

BACKGROUND

In the administration of medicinal liquids using intravenous techniques, it is important and critical to avoid contamination of sterile devices used in the administration of the fluids and to avoid the occurrence of accidental needle sticks which at the very least causes pain and discomfort and can spread infection, etc. In particular, not only are the patients at risk throughout the administration of intravenous therapy due to accidental needle sticks but also, the care giver and other individuals are exposed to considerable risks unless appropriate safety precautions are followed at all times.

Based on the need to provide a safer administration system, there has been a trend in the health care industry toward the reduction and elimination of steel needles in connection with intravenous therapy. In some products instead of using a steel needle to penetrate a port of a catheter which has been installed at a target, select access point along a patient's body, the products use a variety of plastic coupling members for placing the catheter in communication with a conduit, etc.

FIG. 1 shows a conventional infusion bag 10 that has a flexible body 20 that includes a closed top edge 22 and a bottom edge 24. The bottom edge 24 includes a first port 30 for injecting fluids, such as infusion fluid and other additives (e.g., vitamins) into an interior of the bag 10. The bottom edge 24 includes a second port 40 that is in communication with the interior of the bag 10. The second port 40 is also commonly referred to as a spike port and serves as the port through which the contents of the bag 10 are discharged as when an infusion line (conduit) that attaches to a patient is sealingly coupled to the second port 40. The bag 10 can also include a transfer line or fill leg 50 through which ingredients can be added to the bag 10 under some application, such as when compounding total parenteral nutrition (TPN). As is known, TPN is the practice of feeding a person intravenously, bypassing the usual process of eating and digestion. The person receives nutritional formulas containing salts, glucose, amino acids, lipids and added vitamins.

There are a number of deficiencies with the construction of bag 10. First, air must be removed from the body 20 of the bag 10 prior to sending the bag 10 out to a patient. This is called "airing" the bag 10. This is a very tedious process that requires the bag 10 to be turned upside down so that the bottom edge 24 and the ports 30, 40, 50 face up and the bag 10 is shaken to get the air to go to one side or the other side. A needle is then inserted into one of the ports, such as port 30, and the air is removed. Unfortunately and disadvantageously, this frequently requires numerous sticks as air tends to collect around the ports 30, 40, 50. The second disadvantage of the bag construction occurs when the patient is required to add vitamins or other additives to the bag 10 prior to injecting the contents (e.g., infusion fluid). This requires the patient to attach a needle to a syringe or the like prior to injecting the contents. One will appreciate that in both instances, the technician and the patient him or herself are at risk for needle sticks due to the use of needles to perform both operations.

There is thus a perceived need for an improved infusion bag construction that overcomes the both disadvantages associated with conventional infusion bags and eliminates the risk of needle sticks when "airing" the bag and when injecting additives to the bag.

SUMMARY

An infusion bag according to one exemplary embodiment includes a body having an interior space for holding a fluid. The interior space is defined by a pair of side walls and an inner wall and an opposite bottom wall. The inner wall extends across the body from one side wall to the other side wall such that a first angle $\alpha 1$ is formed between a first end of the inner wall and one side wall and a second angle $\alpha 2$ is formed between a second end of the inner wall and the other side wall. The first angle is different from the second angle. The bag also includes a needleless port that is in fluid communication with the interior and is configured to sealingly mate with an external device. The needless port is disposed in an upper corner of the body where the second end of the inner wall intersects the other side wall.

In another embodiment, an infusion bag includes a body having an interior space for holding a fluid. The interior space is defined by a pair of side walls and an inner wall and an opposite bottom wall. The inner wall extends across the body from one side wall to the other side wall defining an asymmetrically top interior space and the body has an opening formed in a top corner of the body at an offcentered location for hanging the bag at an angle. The bag also includes a needleless port that is in fluid communication with the interior and is configured to sealingly mate with an external device. The needleless port includes a web portion through which a stem extends and is in fluid communication with the interior space at a first end thereof. The stem has an opposite second end that mates with an external connector of the needleless port that is located proximate the other side wall. The stem is formed at angle other than 90 degrees with respect to the other side wall from which the needleless port extends outwardly therefrom.

In another embodiment, an infusion bag includes a body having an interior space for holding a fluid, the interior space being defined by a pair of side walls and an inner wall and an opposite bottom wall. The inner wall extends across the body from one side wall to the other side wall. The bag also includes a needleless port that is in fluid communication with the interior and is configured to sealingly mate with an external device. The needleless port is formed at a top corner of the body along a seam of where the side walls are sealingly joined together. The needleless port is formed with respect to the side wall such that a longitudinal axis of the needleless port defines an angle that is less than 50 degrees as measured from the side wall.

These and other aspects, features and advantages shall be apparent from the accompanying Drawings and description of certain embodiments of the invention.

DETAILED DESCRIPTION OF CERTAIN EMBODIMENTS OF THE INVENTION

Figure 2:
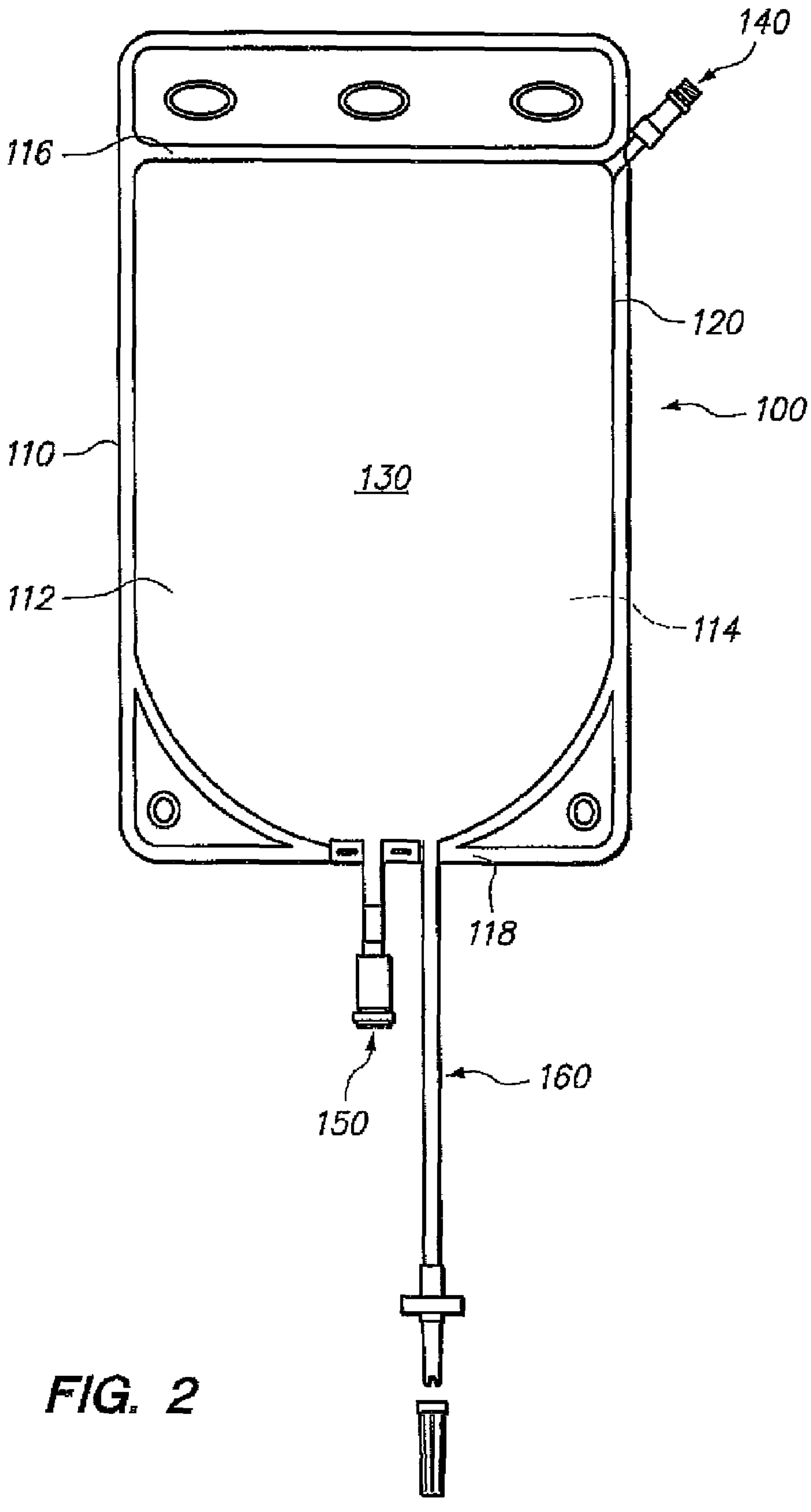
FIG. 2 is a side elevation view of an infusion bag with needleless access port in accordance with a first embodiment.

FIG. 2 is a side elevation view of an infusion bag 100 according to a first embodiment of the present invention. The infusion bag 100 includes a body 110 that is formed of a flexible material. The body 110 has a first side or face 112, a second side or face 114, a top edge 116, and an opposite second edge 118. In addition, the first and second sides 112, 114 of the body 110 is defined by and sealed along a pair of side edges 120. The body 110 includes an interior 130 which receives and stores contents that are later discharged from the bag 100. The interior 130 is defined between the top edge 116, bottom edge 118 and side edges 120.

In accordance with the first embodiment of the present invention, the bag 100 includes at least one needleless port 140 that is in fluid communication with the interior 130 of the bag 100. The needleless port 140 can be formed of any number of different types of needleless coupling members that permit another member or piece of equipment of the infusion delivery system to be sealingly and securely attached to the needleless port 140. For example, the needleless port 140 can be either a male or female coupling member that is constructed and configured to interlockingly and sealingly mate with a complementary female or male coupling member that is part of a component, such as a conduit or line, that is intended to be sealingly attached to the needleless port 140.

In one embodiment, the needleless port 140 is a valve commercially available from Halkey-Roberts under the trade name Robertsite® Needlefree valve. In particular, one suitable valve is a Halkey-Roberts Swabable Valve that is formed of three parts including a female body, a sealing stem, and a male body, all of which are sonic welded together. It will be appreciated that other types of valves can be used as the needless port 140 so long as they permit the desired fluid, sealed connection between the bag and another component, such as a syringe or a line (e.g., vent line).

In one embodiment, the needleless port 140 is part of a luer type connection system. A luer type connection system typically consists of round male and female interlocking tubes, slightly tapered to hold together better with even just a simple pressure/twist fit. The luer connections can either be just that ("luer slip"), or can have an additional outer rim of threading (a "luer lock"), allowing them to be far more secure. For example and as shown, the needless port 140 can be the male half of a luer connector, which can fit into both a female luer slip or luer lock male connector. The illustrated needleless port 140 is in the form of luer lock male connector.

It will also be understood that the needleless port 140 can be the female half of a luer connector, which can fit onto both a luer slip or luer lock male connector that is part of a component that is to be attached to the bag 100 (e.g., a device for supplying an additive to the contents of the bag). When the male connector is a luer slip, the tip of it simply inserts into the female half of the connector. When the male connector is a luer lock, which is the same as the luer slip but adds the threaded rim, the inner nipple thereof still inserts inside the female half, but the rim around the base of the female half screws into the rim, thereby locking it in place.

Accordingly, in one embodiment, the needleless port 140 is a luer lock type connector, such as a male or female luerlock, a Smart Site type connector, a Halkey-Roberts connector, or a Heplock/PRN adapter needle port. The needleless port 140 thus can be in the form of a connector has a stem portion that protrudes outwardly from the bag 100 and permit the user to grasp and manipulate the connector in order to sealingly connect the port 140 to a mating connector that is typically part of a conduit or line for delivering fluid to the bag 100 or in the case of venting the bag 100, the use of a complimentary connector may not be necessary or in the case that it is necessary, the complimentary connector permits venting of air from the interior of the bag 100.

In the first embodiment, the needleless port 140 is located in a corner of the bag 100. More particularly, the needleless port 140 is a located along the top edge 116 where the top edge 116 and side wall 120 join one another. In other words, the needleless port 140 is located in one of the top corners of the bag 100. The needleless port 140 directly communicates with the interior 130 of the bag 100 to permit fluid to be either removed or added to the interior 130. For example, a syringe containing an additive, such as one or more vitamins, and including a luer type connector at its distal end, can be coupled to the needleless port 140. The syringe is then manipulated as by moving a plunger thereof, resulting in the additive being injected into the interior 130.

The additive(s) that is added through the needleless port 140 can be any number of different types of additives, including but not limited to, vitamins, antibiotics, folic acid, insulin, etc.

The illustrated bag 100 includes one port 150 that is intended to be connected to a conduit or the like that is in attached at the other end to a device for administering the stored fluid in the interior 130 to the patient. The port 150 can be in the form of a standard spike port that is intended to mate with a spike that is part of a conduit or line that is used to discharge the fluid from the interior 130 of the bag 100 and to the patient. The port 150 is typically not a needleless port since the spike device that mates with the port 150 has a sharpened end. Conventionally, the spike is mated with the spike port 150 by removing the protective tab from the spike port and a protective cover is removed from the spike itself. The set spike is held at a straight-on angle to the bag so that it is parallel to the bag walls as it is inserted. Next, the spike is firmly inserted into bag at a straight-on angle until the spike is fully seated. The port 150 is thus not a luer type connector as in the needleless port 140.

It will therefore be understood that the port 150 can constitute the primary means that the fluid contained in the interior 130 is discharged from the interior 130. It will also be appreciated that the port 150 can be constructed to have a needleless construction similar to the needleless port 140. In addition, the needleless port 140 can constitute the primary means for injecting the primary ingredients (stock infusion fluid) into the interior 130.

In the instance of where the bag 100 is of a total parenteral nutrition (TPN) type, the bag 100 includes a transfer line or fill leg 160 that is in communication with the interior 130 of the bag 100 and can be used to add additional components to the interior. For example, the fill leg 160 can be in the form of a stem or flexible conduit that extends outwardly from the bag 100 and permits the user to sealingly connect a device to the fill leg 160 for adding a substance. It will be appreciated that the inclusion of a fill leg 160 in the bag 100 finds particular utility when compounding total parenteral nutrition (TPN) compositions.

Once again, the fill leg 100 is not of a needleless type construction and is not a required component of the bag 100.

In other words, it will be appreciated and understood that the present invention is not limited to being incorporated only with TPN type bags; but instead, the bag 100 can be a simple infusion bag design that does not incorporate the fill leg 160. In this embodiment, the bag 100 only includes the needleless port 140 and the port 150 or as discussed below, the bag can only include the needleless port 140.

Accordingly, the bag 100 of the present invention offers a number of advantages due to the needleless port 140 that is constructed as a means for injecting an additive into the interior 130 of the bag 100 or for removing fluid, e.g., venting of air. The bag 100 thus provides easy air removal for prefilled and empty containers (bags 100). In addition, medication safety, insuring the concentration of additives or medications will not exceed desired concentrations because of the distance between the medication/additive port 140 and the spike port 150.

Figure 3:
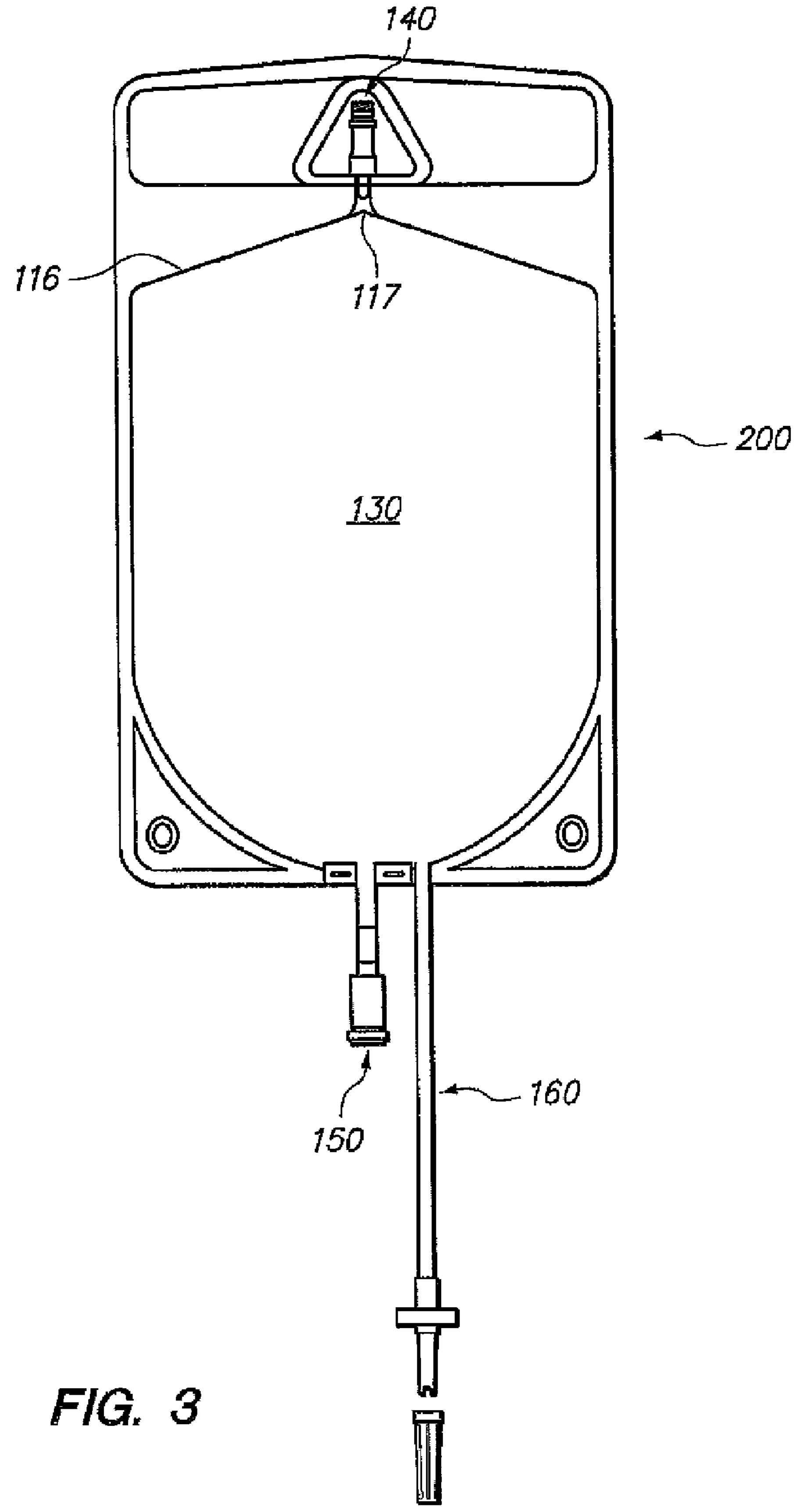
FIG. 3 is a side elevation view of an infusion bag with needleless access port in accordance with a second embodiment.

FIG. 3 illustrates a bag 200 according to another embodiment of the present invention. The bag 200 has a construction that is similar to the bag 100 except that in this embodiment, the needleless port 140 is not located in one or the top corners of the bag 100 but instead is located in a middle or center portion 117 of the upper edge 116 of the body 110. Thus, the needleless port 140 is located in a top center position of the bag 100.

The construction of the needleless port 140 is the same as in the bag 100 in that it is preferably, a luer type connector.

In both bags 100, 200, the needleless port 140 is located along the top edge 116 and therefore, the fluid that is added to the interior 130 through the needleless port 140 flows by gravity within the interior of the bag 100. This allows an improved mixing of the additives with the primary fluid (e.g., infusion fluid) contained in the interior 130 of the bag 100.

Figure 1:
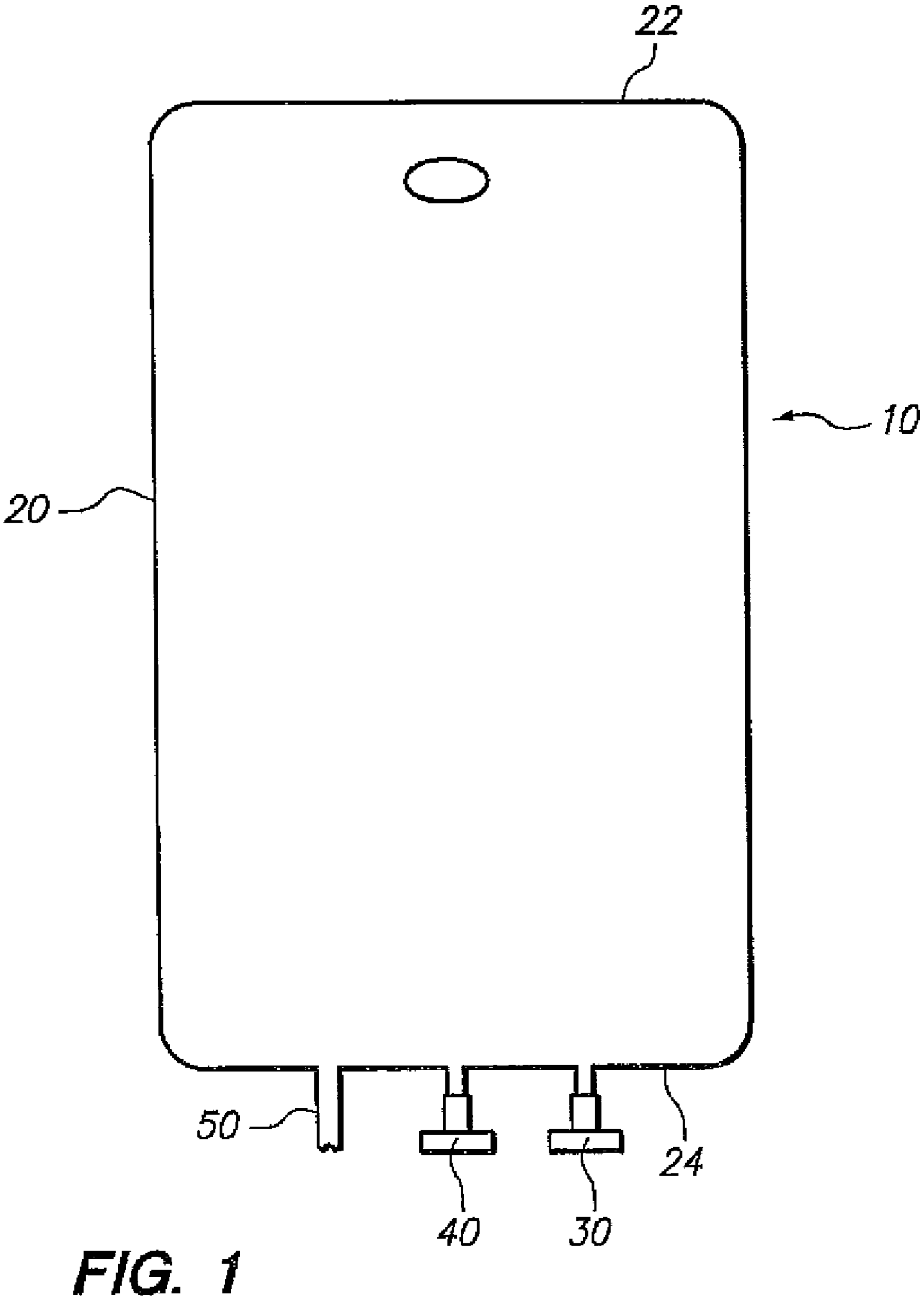
FIG. 1 (PRIOR ART)
FIG. 1 is a side elevation view of a conventional infusion bag.

Once again, the bag 200 includes the port 150, such as a spike port, and optionally includes the fill leg 160 as described in detail with reference to the embodiment of FIG. 1.

Figure 4:
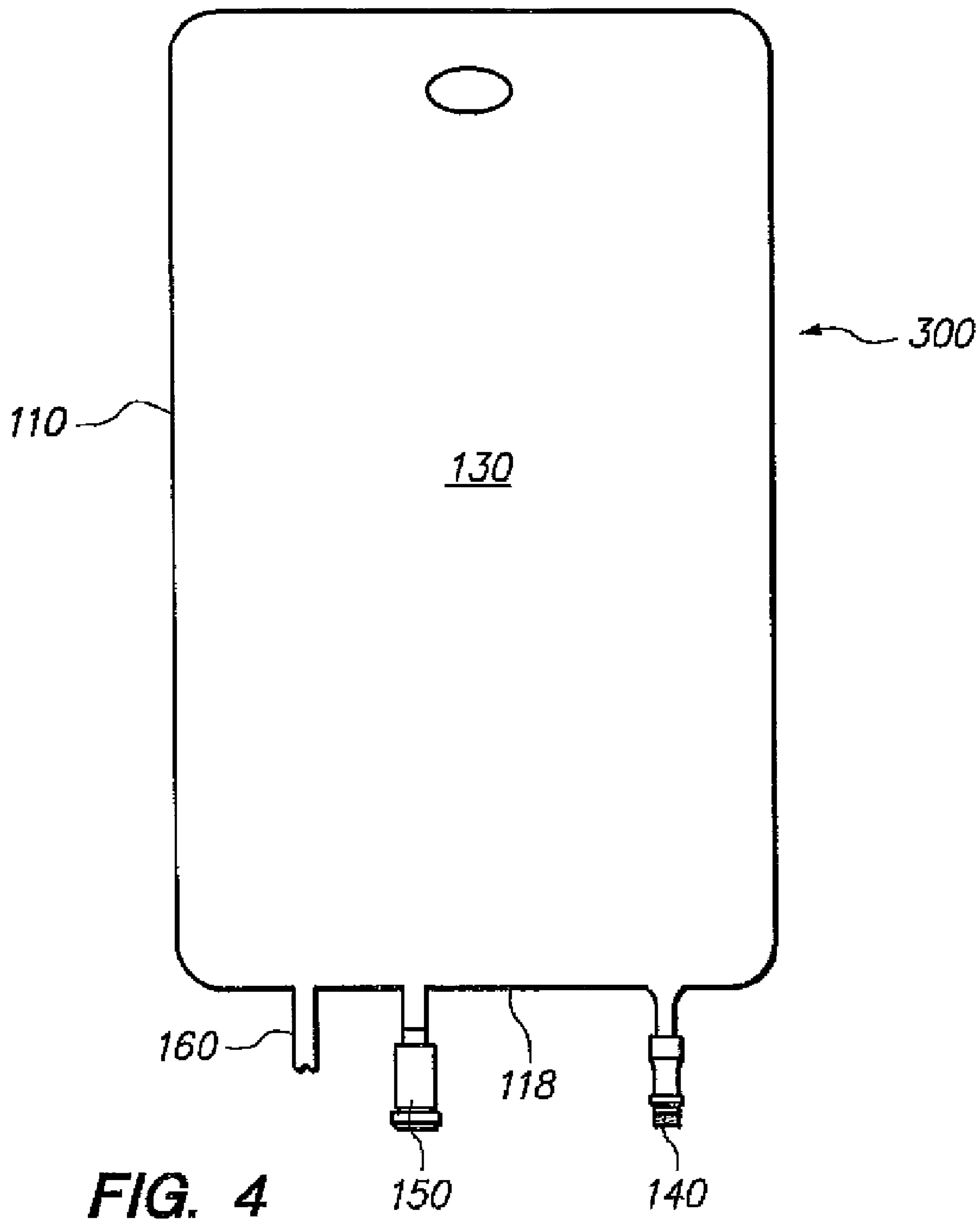
FIG. 4 is a side elevation view of an infusion bag with needleless access port in accordance with a third embodiment.

Now referring to FIG. 4, a bag 300 that is similar to bags 100, 200 is illustrated. In this embodiment, the needleless port 140 is formed along the bottom edge 118 of the body 110 of the bag 100 adjacent the port 150. Optionally, the fill leg 160 is also provided and formed along the bottom edge 118 of the body 110. In this embodiment, both the primary means for adding an additive (e.g., the needleless port 140) and the primary means (e.g., the spike port 150) for discharging the contents of the bag 100 are located along the bottom edge 118.

The needleless port 140 of this embodiment can have the same construction as in the embodiments of FIGS. 2 and 3 and offers the same advantages.

Figure 5:
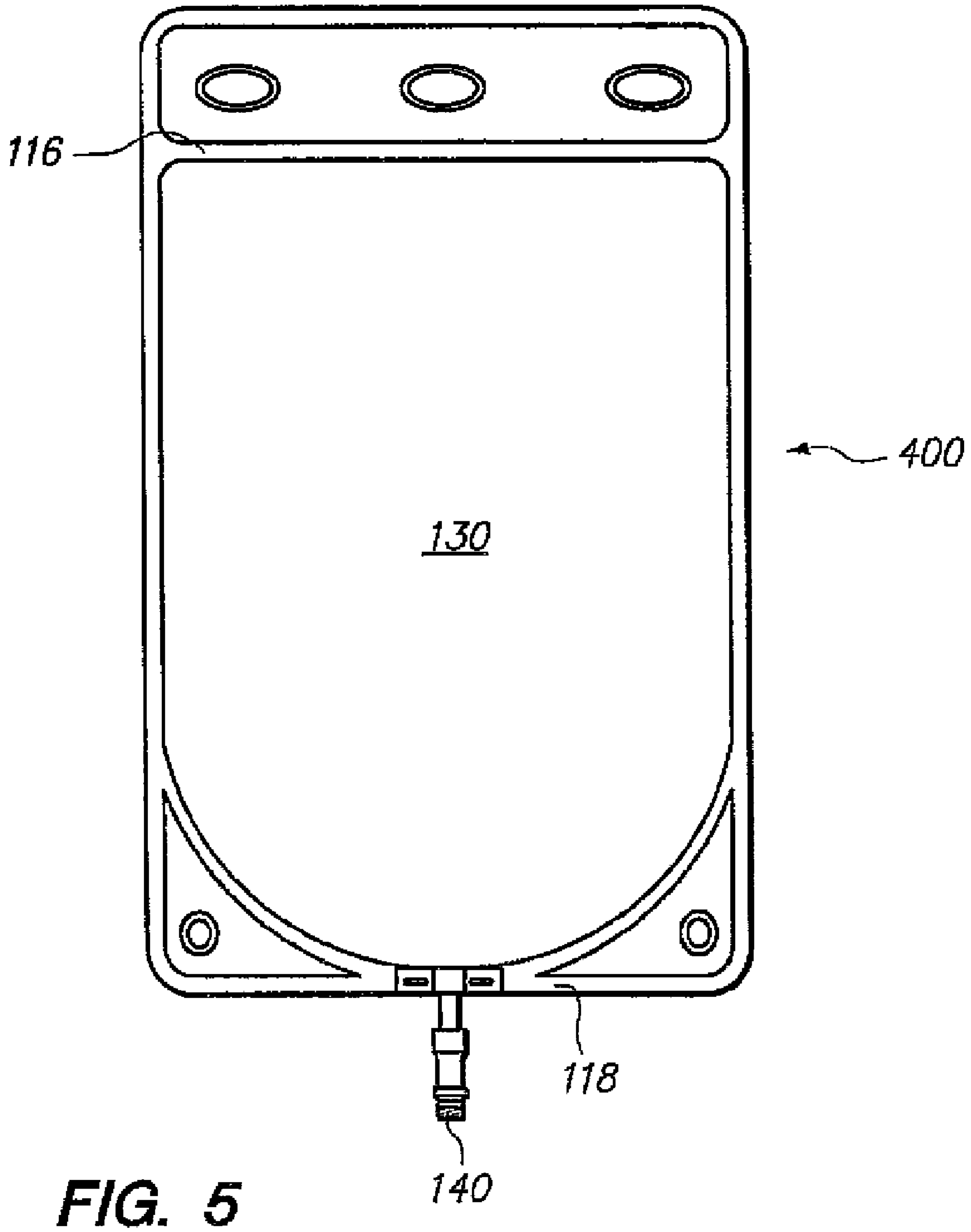
FIG. 5 is a side elevation view of an infusion bag with needleless access port in accordance with a fourth embodiment.

FIG. 5 illustrates a bag 400 in accordance with another embodiment of the present invention. The bag 400 is similar to the other bags disclosed herein but in this embodiment, the bag 400 only includes one access port, namely, the needleless access port 140. The needleless access port 140 is formed along the bottom edge 118 of the bag 400 and is designed to perform a number of different functions since there is only one access port. More specifically, the needleless access port 140 has one end that opens into the interior 130 of the bag 400 and includes another end that is constructed to be sealingly coupled to another member, such as a conduit or line. The other end represents the luer connector component of the needleless access port 140 as discussed above.

In the bag 400, the needleless port 140 not only serves as the means for airing the bag 400 both prior to and after liquid has been injected into the bag 400 and for injecting additives, such as vitamins, as discussed above but also, the needleless port 140 serves as the means for delivering the primary ingredients to the bag 400 and also the needleless port 140 serves as the means for discharging the contents of the bag 400 to the patient. For example, a fill line (conduit/tubing) can be attached to the needleless port 140 for filling the interior 130 with fluid (e.g., infusion fluid) and once the bag 400 is filled, the fill line is then removed from the needleless port 140. If the additive is to be injected into the bag 400 after the primary ingredients are added, a separate conduit or line or other device can be attached to the needleless port 140 for injecting the additive.

Thus, the needleless port 140 is used to not only fill the bag 400 with its contents but is also used to air the bag 400 and also as the means for discharging the contents from the bag 400 to the patient.

While the needleless port 140 is shown as being in the center or middle of the bottom edge 118 of the bag 400, it will be understood that this location is merely exemplary and that the needleless port 140 can be located in any number of other locations, including along the top edge 116 and in any of the four corners (two upper corners and two lower corners) of the bag 400.

Figure 6:
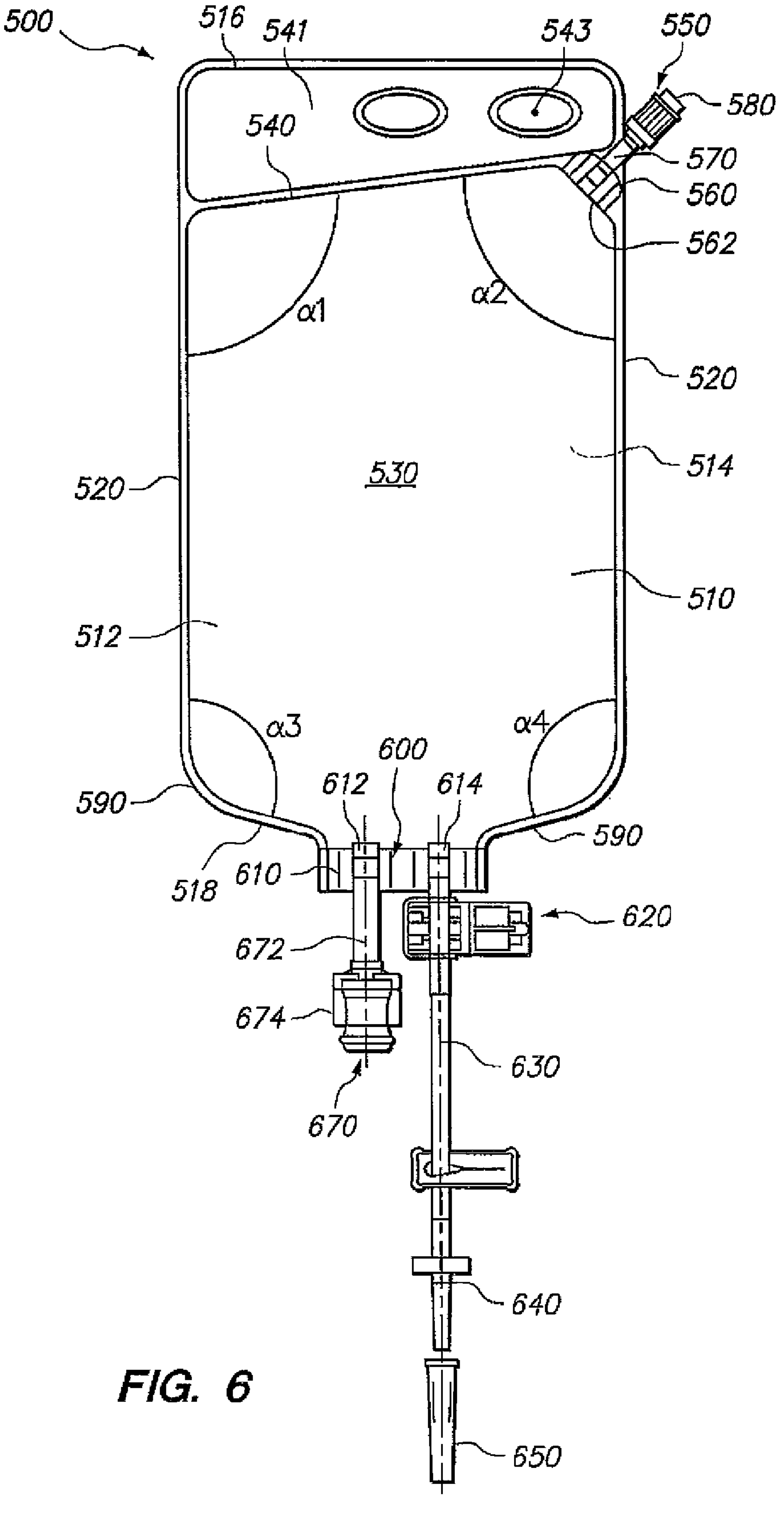
FIG. 6 is a side elevation view of an infusion bag with needleless access port in accordance with a fifth embodiment.

FIG. 6 is a side elevation view of an infusion bag 500 according to a fifth embodiment of the present invention. The infusion bag 500 includes a body 510 that is formed of a flexible material (such as a plastic as in each of the other embodiments). The body 510 has a first side or face 512, a second side or face 514, a top edge 516, and an opposite bottom edge 518. In addition, the first and second sides 512, 514 of the body 510 is defined by and sealed along a pair of side edges 520. The body 510 includes an interior 530 which receives and stores the contents that are later discharged from the bag 500. In contrast to some of the previous embodiments, the bag 500 includes an inner edge 540 that actually defines the top of the interior 530 and is spaced below the top edge 516 which merely defines the topmost edge of the infusion bag 500. The side edges 520 are typically parallel to one another and are generally perpendicular to the top edge 516.

In accordance with this embodiment, the inner edge 540 is not parallel to the top edge 516 but rather is at an angle relative to the side edges 520. More specifically, a first angle $\alpha 1$ is defined between one end of the inner edge 540 and the side edge 520 and a second angle $\alpha 2$ is defined between the other end of the inner edge 540 and the other side edge 520. Since the inner edge 540 is not perpendicular to the side edges 520, the angles $\alpha 1$ and $\alpha 2$ are not equal to one another but rather $\alpha 1$ is greater than $\alpha 2$. In one embodiment, $\alpha 1$ is less than 100 degrees.

Between the inner edge 540 and the top edge 516, the bag 500 includes a space 541 which can serve as a location for an individual to grasp and hold the bag 500. As shown in FIG. 6, the bag 500 can include one or more openings 543 that are used when hanging the bag 500 on a post or like or the opening 543 can be used to grasp and hold the bag 500. Unlike conventional infusion bags, the opening 543 is formed offcentered and in particular, one opening 543 is formed in the right corner of the bag 500. It will be appreciated that if the bag 500 is hung by using the opening 543 in the right corner, the bag 500 will hang at an angle (with the left corner of the bag 500 hanging lower than the right corner). In addition, another opening 543 can be formed in the center of the bag 500.

In accordance with one embodiment of the present invention, the bag 500 includes at least one needleless port 550 that is in fluid communication with the interior 530 of the bag 500. The needleless port 550 can be formed of any number of different types of needleless coupling members that permit another member or piece of equipment of the infusion delivery system to be sealingly and securely attached to the needleless port 550. For example, the needleless port 550 can be of the same type described in reference to needleless port 140. The needleless port 550 can be either a male or a female coupling member that is constructed and configured to interlockingly and sealingly mate with a complementary female or male coupling member that is part of a component, such as a conduit or line, that is intended to be sealingly attached to the needleless port 550.

In the illustrated embodiment, the needleless port 550 is located in a corner of the bag 500. More particularly, the needleless port 550 is located along the inner edge 540 where the inner edge 540 and one side wall 520 join one another. Due to the spacing and offsetting of the inner edge 540 from the top edge 516, the needleless port 550 is located along the side wall 520 below the top edge 516. In the illustrated embodiment, the needleless port 550 is located in the top corner (upper right corner) of the bag 500 that is defined by α2.

The needleless port 550 is formed of a number of different parts or segments. More specifically, the needleless port 550 includes a web portion 560 that extends between the inner edge 540 and the one side wall 520. The web portion 560 is simply a section of the same material that forms the bag 500 where the first side or face 512 is joined to the second side or face 514. The web portion 560 includes an opening 562 that extends therethrough and forms an entrance into the interior 530. The needleless port 550 also includes a hollow conduit 570 that extends through the opening 562 of the web portion 560 and is in fluid communication with the interior 530 to permit fluid either to enter the interior 530 or to exit (be discharged) the interior 530. An opposite end of the conduit 570 is exposed and accessible along the side wall 520 and interfaces with a needless injection port 580 that is located adjacent the side wall 520. For example, a syringe containing an additive, such as one or more vitamins, and including a complementary connector at its end can be coupled to the needleless port 580. The syringe is manipulated resulting in the additive being injected into the interior 530. Alternatively, as described above, the needleless port 580 can be used to vent the interior 530.

In the illustrated embodiment, a central axis of the conduit 570 is at a 45 degree angle with respect to the side wall 520. Accordingly, the needleless injection port 580 is also disposed at a 45 degree angle with respect to the side wall 520. This permits a physician to easily access and connect the needleless injection port 580 to another member, such as a fluid line for injecting a fluid or for removing a fluid from the interior 530 as described above with respect to the other embodiments. By positioning the needleless injection port 580 slightly below the top edge 516, it does not interfere with the hanging or handling of the bag 500. In addition, the combination of the diagonally oriented inner edge 540 and the diagonally oriented conduit 570 results in superior fluid flow both to the needleless injection port 580 as in the case of airing the bag and from the injection port 580 as in the case of injecting or adding a fluid (e.g., additive) to the bag.

In one embodiment, the angle α1 between one side wall 520 and the inner edge 540 is about 98 degrees. Applicant has discovered that the provision of the inner edge 540 in the configuration and orientation shown in FIG. 6 provides a number of advantages and increases the performance of the infusion bag 500. In particular, the configuration of the inner edge 540 encourages air within the interior 530 to flow toward the upper right hand corner where the needleless port 550 is located. This is advantageous since the needleless port 550 is intended, in one role, to act as the port through which air is vented from the interior 530 of the bag 500. Thus, air is effectively directed toward the needleless port 550 as a result of the design of the inner edge 540. This reduces the time needed to effectively vent the interior 530 and further, reduces the chance that pockets of air may remain within the interior 530 after the venting process. In conventional infusion bags, the top edge is not a diagonal edge relative to the sides but rather is perpendicular to the two side edges.

By forming the opening 543 in the upper right corner, airing of the bag 500 is also improved since the bag 500 hangs at an angle with the left side being positioned lower than the right side. Since the upper right corner is where the needleless port 550 is positioned and the bag 500 includes the inner edge 540, air flows toward the needleless port 550 where it is vented. The arrangement of these features forces air to the location of where the needleless port 550 is located.

The bag 500 also includes a bottom edge 590 that represents the bottom of the infusion bag 500. The bottom edge 590 generally tapers inwardly and downwardly from the side edges 520 toward a central port section 600. An angle α3 is defined between one side edge 520 and the bottom edge 590 and an angle α4 is defined between the other side 520 and the bottom edge 590. In one embodiment, angle α3 is about equal to α4. For example, each of angles α3 and α4 is about 109 degrees.

The bag 500 can also include one or more additional ports and in particular, the illustrated bag 500 includes a set of ports located within the central port section 600. For example, the central port section 600 includes a web section 610 defined by the joined first and second sides 512, 514. The web section 610 includes second and third openings 612, 614, respectively, that pass therethrough and form entrances into the interior 530 and extend below the bottom edge 590 at the opposite ends.

For example, the bag 500 can include a second port 620 that is intended to be connected to a conduit or the like that is attached at the other end to a device for delivering, according to one application, a fluid to the interior 530 to the patient. In particular, the port 620 includes a conduit 630 that extends through the web section 610 and is open at an inner end so as to form an entrance into the interior 530. The conduit 630 is thus a hollow member that is in fluid communication with the interior 530. In addition, the conduit 630 is coupled at the other end to a spike 640. The spike 640 can be fitted into the end of the conduit 630 to provide a connector for allowing another device to be placed in fluid communication with the interior 530. The spike 640 can be covered with a removable protective cap 650. The protective cap 650 can be in the form of a plastic cap that can be fitted over the spike 640 to cover and protect the opening formed in the cap 650.

Other accessories, such as clamps, 660 can be provided along the conduit 630 for restricting flow through the conduit 630.

It will be understood that the free end of the spike 640 that is accessible once the protective cap 650 is removed can be sealingly attached to a conduit or the like or a device, e.g., a syringe, that can administer fluid (e.g., primary ingredients—stock infusion fluid) into the interior 530.

In the instance of where the bag 500 is of a total parenteral nutrition (TPN) type, the second port 620 is part of a transfer or fill line leg that is in communication with the interior 530 of the bag 500 and can be used to add additional components to the interior 530.

The bag 500 can also include a third port 670 that is intended to be connected to a conduit or the like that is attached at a free end to a device for administering the stored contents in the interior 530 to a patient. The third port 670 can be in the form of a standard spike port that is intended to mate with a spike that is part of a conduit or line that is used to discharge fluid from the interior 530 of the bag 500 and to the patient. The third port 670 is formed of a conduit 672 that extends through the web section 610 and is open at an inner end so as to form an entrance into the interior 530. The conduit 672 is thus a hollow member that is in fluid communication with the interior 530. In addition, the conduit 672 is coupled at the other end to an outlet port 674.

The third port 670 is typically not a needleless port since the spike device that mates with the outlet port 674 has a sharpened end. Conventionally, the spike is mated with the outlet port 674 by removing any protective covering from the outlet port 674 and by removing the protective covering from the spike device. The spike is held straight on and is then firmly inserted into the bag 500. It will be appreciated that the outlet port 674 can constitute the primary means that the fluid contained in the interior 530 is discharged therefrom. It will also be appreciated that the outlet port 674 can be constructed to have a needleless construction similar to those described above. Further, the outlet port 674 can constitute the primary means for injecting the primary ingredients (e.g., stock infusion fluid) into the interior 530.

As with the previous embodiments, the bag 500 offers a number of advantages due to the needleless port 550 that is constructed as a means for injecting an additive into the interior 530 of the bag 500 or for removing fluid, e.g., venting of air. The bag 500 thus provides easy air removal for prefilled and empty containers (bags 500). In addition, medication safety, insuring the concentration of additives or medications will not exceed desired concentrations because of the distance between the medication/additive port 550 and the third port 670.

In addition, by placing the needleless port 550 in an upper corner, additives that are added therethrough to a stock solution or the like have better diffusion properties since the additives flow downwardly in the stock solution to the discharge port. This arrangement allows the additives a greater opportunity to mix with the base (stock) solution prior to being discharged through a port that is located along the bottom edge of the bag 500.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. An infusion bag comprising:

a body having a top wall and a single interior space for holding a fluid, the interior space being defined by a pair of parallel side walls and an inner wall and an opposite non-planar, tapered bottom wall, the inner wall extending across the body from one side wall to the other side wall such that a first angle $\alpha 1$ is formed between a first end of the inner wall and one side wall and a second angle $\alpha 2$ is formed between a second end of the inner wall and the other side wall, the first angle being different from the second angle, wherein inner surfaces of the parallel side walls are planar from the top wall to the bottom wall and the interior space is continuous and uninterrupted from the inner wall to the bottom wall across the entire width of the body;

a needleless port that protrudes outwardly from the other side wall, below the top wall, and is in fluid communication with the interior and is configured to sealingly mate with an external device, the needleless port being configured and positioned within the body for both delivering a fluid to the interior space and for alternatively airing the interior space, wherein the needleless port is disposed in an upper corner of the body where the second end of the inner wall intersects the other side wall, wherein the angled inner wall and location of the needleless port combine to promote airing of the bag through the needleless port; and at least one other port that is in at least selective communication with the interior space and is located along the bottom wall, wherein each port formed along the bottom wall is located entirely below locations where the parallel side walls intersect and join the bottom wall;

wherein the body has only two openings formed in the body for hanging the bag, the two openings being formed in an asymmetric manner across a width of the body, with one opening being formed proximate the second top corner of the body at an offcentered location for hanging the bag at an angle to promote airing of the bag, wherein the other opening is formed in a center of the body such that the body is free of an opening in a location proximate the first top corner so as to prevent the bag from being hung by the first top corner.

2. The infusion bag of claim 1, wherein the needleless port includes a web portion through which a conduit extends and is in fluid communication with the interior space at a first end thereof, the conduit having an opposite second end that mates with an external connector of the needleless port that is located proximate the other side wall.

3. The infusion bag of claim 2, wherein $\alpha 2$ is less than $\alpha 1$.

4. The infusion bag of claim 3, wherein $\alpha 1$ is about 98 degrees.

5. The infusion bag of claim 2, wherein the second end of the inner wall intersect the other side wall at location higher than the location where the first end of the inner wall intersects the one side wall so as to position in the upper corner that is closer to a top edge that defines the topmost section of the body.

6. The infusion bag of claim 5, wherein the external connector is located below the top edge.

7. The infusion bag of claim 2, wherein the conduit of the needleless port is defined by a central axis that forms a 45 degree angle with respect to the other side wall.

8. The infusion bag of claim 1, wherein the inner wall is formed at angle with respect to the two side walls that causes air collected in the interior space to flow in a direction upwardly and toward the needleless port where it can be vented, wherein an angle defined between a central axis through the needleless port and the side wall is an angle other than 90 degrees.

9. The infusion bag of claim 1, wherein the body has a first top corner where the one side wall joins the top wall and a second top corner where the other side wall joins the top wall, the body having a plurality of openings formed in the body between the top wall and the inner wall for hanging the bag, the openings being formed in an asymmetric manner across a width of the body, with one opening being formed in proximate the second top corner of the body at an offcentered location for hanging the bag at an angle to promote airing of the bag, wherein the body is free of an opening in a location proximate the first top corner so prevent the bag from being hung about the first top corner.

10. The infusion bag of claim 1, wherein the top wall of the body is continuous and uninterrupted along its length and is free of any connectors.

11. An infusion bag comprising:

a body having a top wall and an interior space for holding a fluid, the interior space being defined by a pair of side walls and an inner wall and an opposite bottom wall, the inner wall extending across the body from one side wall to the other side wall defining an asymmetrically top interior space, the body having a first top corner where one side wall joins the top wall and a second top corner where the other side wall joins the top wall, the body having only two of openings formed in the body for hanging the bag, the two openings being formed in an asymmetric manner across a width of the body, with one opening being formed proximate the second top corner of the body at an offcentered location for hanging the bag at an angle to promote airing of the bag, wherein the other opening is formed in a center of the body such that the body is free of an opening in a location proximate the first top corner so as to prevent the bag from being hung by the first top corner; and a needleless port that is in fluid communication with the interior and is configured to sealingly mate with an external device, wherein the needleless port includes a web portion through which a stem extends and is in fluid communication with the interior space at a first end thereof, the stem having an opposite second end that mates with an external connector of the needleless port that is located proximate the other side wall, the stem being formed at angle other than 90 degrees with respect to the other side wall from which the needleless port extends outwardly therefrom, wherein the one opening formed in the second top corner of the body is located proximate the needleless port.

12. The infusion bag of claim 11, wherein a first angle $\alpha 1$ is formed between a first end of the inner wall and one side wall and a second angle $\alpha 2$ is formed between a second end of the inner wall and the other side wall, the first angle being different from the second angle.

13. The infusion bag of claim 11, wherein the other opening is formed in the body in a central location between the pair of side walls, with the body being continuous and uninterrupted from the other opening to the side wall that defines the first top corner.

14. The infusion bag of claim 11, wherein the stem is formed in the web that is formed between the one end of the inner wall and other side wall.

15. An infusion bag comprising:

a body having a top wall and an interior space for holding a fluid, the interior space being defined by first and second side walls and an inner wall and an opposite bottom wall, the inner wall extending across the body from the first side wall to the second side wall such that a first angle $\alpha 1$ is formed between a first end of the inner wall and the first side wall and a second angle $\alpha 2$ is formed between a second end of the inner wall and the second side wall, the first angle being greater than the second angle; and a needleless port that is in fluid communication with the interior and is configured to sealingly mate with an external device, the needleless port being formed at a corner of the body where the inner wall and second side wall are joined and along a seam of the body, the needleless port being formed with respect to the second side wall such that a longitudinal axis of the needleless port defines an angle that is less than 50 degrees as measured from the second side wall, wherein the needleless port partitions the second side wall into a top section that is above the needleless port and a bottom section that is below the needleless port, the top section intersecting the top wall and the bottom section intersecting the bottom wall, the top and bottom sections being coplanar, the top and bottom sections both being parallel to the first side wall;

wherein the interior space is continuous and uninterrupted at least along the other side wall from the needleless port to the bottom wall and along the inner wall to facilitate airing of the interior space by promoting air flow within the interior space to the needleless port where the air is vented.

16. The infusion bag of claim 15, wherein the top corner of where the needleless port is located includes a web material that extends between the inner wall and the seam, the needleless port having a conduit that extends through the web material and forms an entrance into the interior space.

17. The infusion bag of claim 15, wherein the needleless port includes a needleless injection port for delivering a fluid to the interior space.

18. The infusion bag of claim 17, wherein the body further includes an exit port that is disposed along the bottom wall and is in fluid communication with the interior space to allow fluid within the interior space to flow from the interior space, the needleless injection port being disposed at an opposite end of the interior space relative to the exit port such that fluid delivered to the interior space through the needleless injection port must flow through from a top end of the interior space to a bottom end where the exit port is located, thereby permitting proper mixing of the delivered fluid with a base stock solution that is present in the interior space before delivery of the fluid through the needleless injection port.

19. The infusion bag of claim 15, wherein the body has a first top corner where the first side wall joins the top wall and a second top corner where the second side wall joins the top wall, the body having only two openings formed in the body between the top wall and the inner wall for hanging the bag, the two openings being formed in an asymmetric manner across a width of the body, with one opening being formed in proximate the second top corner of the body at an offcentered location for hanging the bag at an angle to promote airing of the bag, wherein the body is free of an opening in a location proximate the first top corner so prevent the bag from being hung about the first top corner.

* * * * *